United States Patent
Charles (10) Patent No.: US 9,730,834 B2
(45) Date of Patent: Aug. 15, 2017

(54) VARIABLE STIFFNESS CANNULA AND METHODS FOR A SURGICAL SYSTEM

(71) Applicant: Novartis AG, Basel (CH)

(72) Inventor: Steven T. Charles, Memphis, TN (US)

(73) Assignee: Novartis AG, Basel (CH)

( * ) Notice: Subject to any disclaimer, the term of this patent is extended or adjusted under 35 U.S.C. 154(b) by 157 days.

(21) Appl. No.: 14/136,165

(22) Filed: Dec. 20, 2013

(65) Prior Publication Data

US 2015/0173947 A1 Jun. 25, 2015

(51) Int. Cl.
A61F 9/007 (2006.01)

(52) U.S. Cl.
CPC ...... *A61F 9/00736* (2013.01); *A61F 9/00727* (2013.01)

(58) Field of Classification Search
CPC ............. A61F 9/00736; A61F 9/00754; A61F 9/00727; A61F 2/1662; A61F 9/008; A61B 17/3417; A61B 17/3421; A61B 2017/3456
USPC ................ 606/107, 166–180, 187; 623/6.12; 604/164.12
See application file for complete search history.

(56) References Cited

U.S. PATENT DOCUMENTS

| | | | |
|---|---|---|---|
| 3,890,977 A * | 6/1975 | Wilson | 604/531 |
| 5,273,530 A | 12/1993 | del Cerro et al. | |
| 5,441,496 A * | 8/1995 | Easley | A61F 9/008 604/902 |
| 6,015,403 A | 1/2000 | Jones | |
| 6,413,245 B1 | 7/2002 | Yaacobi et al. | |
| 6,491,670 B1 | 12/2002 | Toth et al. | |
| 6,602,227 B1 * | 8/2003 | Cimino et al. | 604/113 |
| 6,652,491 B1 * | 11/2003 | Walker et al. | 604/164.01 |
| 6,945,984 B2 | 9/2005 | Arumi et al. | |
| 7,141,048 B1 | 11/2006 | Charles | |
| 7,285,107 B1 | 10/2007 | Charles | |
| 7,862,541 B2 * | 1/2011 | Jeffrey et al. | 604/96.01 |
| 7,909,800 B2 | 3/2011 | Cazzini | |
| 8,177,747 B2 | 5/2012 | Pinedjian | |
| 2005/0171507 A1 | 8/2005 | Christian et al. | |
| 2008/0195135 A1 | 8/2008 | Attinger | |
| 2009/0043321 A1 | 2/2009 | Conston et al. | |
| 2011/0112471 A1 * | 5/2011 | Ghannoum | 604/35 |

(Continued)

FOREIGN PATENT DOCUMENTS

WO   2010132751 A1   11/2010

OTHER PUBLICATIONS

Alcon Grieshaber AG, Grieshaber Product Catalog, 2013, 30 pages.
(Continued)

*Primary Examiner* — Eric Rosen
*Assistant Examiner* — Mikail Mannan (57) ABSTRACT

Described herein is an apparatus for treatment of an ocular condition of a patient, comprising a hollow elongate member sized to penetrate an eye of the patient and including a body portion, a distal tip, and a lumen extending though both. The body portion includes a proximal end, a distal end, and a first diameter, and defines longitudinal axis. The distal tip extends from the distal end of the body portion and is arranged to treat tissue in the eye. The distal tip includes an inner tube defining the lumen in part, an outer sheath surrounding the inner tube, and a second diameter. The distal tip is configured to transition between a first rigid orientation and a second less rigid orientation.

16 Claims, 8 Drawing Sheets

(56) References Cited

U.S. PATENT DOCUMENTS

| | | |
|---|---|---|
| 2012/0191064 A1 | 7/2012 | Conston et al. |
| 2014/0025045 A1 | 1/2014 | Abt et al. |
| 2015/0148838 A1 | 5/2015 | Schaller |
| 2015/0164687 A1* | 6/2015 | Kashani ............... A61F 9/0017 |
| | | 604/506 |

OTHER PUBLICATIONS

Gizzard et al., "New Silicone Tipped Cannulas for Subretinal Fluid Drainage," British Journal of Ophthalmology, 1989, 73, 838-839.
MedOne Brochure, "Exactly What Your Looking For—High Quality Instruments for Vitreoretinal Surgery," 2012, 12 Pages.
Flynn et al. "Design Features and Surgical Use of a Cannulated Extrusion Needle," Graefe's Arch Clin Exp Ophthalmol (1989) 227:304-308, 5 pages.
McLeod et al. "Modified Charles flute needle," British Journal of Ophthalmology, 1981, p. 69.
Alcon Grieshaber Catalog, Copyright 2004, pp. 17-18.

* cited by examiner

VARIABLE STIFFNESS CANNULA AND METHODS FOR A SURGICAL SYSTEM

BACKGROUND

Cannulas are one example of microsurgical instruments used in ophthalmic surgical procedures, such as retinal detachment surgery, to aspirate fluids such as blood, aqueous humor, and/or balanced saline solutions (BSS) referred to as infusion fluid. These cannulas are typically connected by tubing to the machine-induced vacuum source and the fluids are collected in a disposable cassette (e.g., at a control console). For ophthalmic surgical procedures, it is important that the cannula tip be specially designed for the delicate eye area. For example, some cannula tips are formed with a soft, compliant tip formed from a transparent soft material (e.g., such as silicone). The soft tip helps prevent damage to the delicate tissue of the eye in the event of physical contact with the eye, typically the retina.

Retinal detachment is a serious eye condition that, if not treated early, may lead to impairment or loss of vision. The retina is a fine layer of nerve cells that covers the inside back portion of the eye. If the retina thins, one or more tears or holes in the retina may result, leading to retinal detachment. Retinal detachment is caused by shrinkage of the vitreous. The vitreous is a clear, gel-like substance that fills the inside of the eye and is firmly attached to the retina especially near the periphery. As the vitreous shrinks, as a result of age, inflammation, injury or near-sightedness, it often separates from the retina and, in some cases, it may pull a piece of the retina away with it, leaving a tear or hole in the retina. If the retina tears or breaks, watery fluid from the vitreous may pass through the hole and flow between the retina and the back wall of the eye producing "subretinal" fluid. Over time, the flow of the vitreous fluid between the retina and the back of the eye separates the retina from the back of the eye and causes it to detach.

Some ophthalmic procedures require a soft-tipped microsurgical instrument that minimizes inadvertent injury to the delicate structures within the eye. During certain ophthalmic procedures (e.g., retinal tear, retinal detachment, and/or vitreoretinal procedures), for example, the tip of a cannula may be used to manipulate the retina, to fill the vitreous cavity with air or gas, and/or more commonly to remove blood, subretinal fluids, or intravitreal fluids. If the flow of vitreous fluid under the retina through retinal breaks or holes has caused the retina to detach, the detached portion of the retina may need to be reattached by draining subretinal fluid from under the retina to allow the retina to be replaced into its anatomically correct position.

During posterior segment surgery, the surgeon typically uses several different instruments throughout the procedure. This frequently requires that these instruments be repeatedly and/or sequentially inserted into and removed out of the incision. To guard against trauma to the incision site from the repeated entry/exit of instruments, surgeons generally insert the instruments through cannulas consisting of a narrow tube with an attached hub. The surgeon typically makes an incision on the eye (e.g., with a trocar through the sclera) and inserts the tube of the cannula through the incision up to the hub, which acts as a stop that prevents the tube from entering the eye completely. Valved cannulas were developed to address the issue of fluids flowing out of the tube when the tube is not connected to an infusion device, or when an instrument is not inserted within the tube because the interior of the eye is pressurized. In some instances, valved cannulas include a slit silicone diaphragm or cap on the outside of the hub. The slit provides an opening into the tube through which the surgical instrument can be inserted. However, a soft-tipped cannula may be insufficiently rigid to effectively open the slit without the application of undue pressure against the cannula. Thus, surgeons frequently need to use a more rigid instrument to open the slit before advancing a conventional soft-tipped cannula through the slit into the cannula.

Accordingly, there exists a need for an improved instrument configured for "soft-tipped" use while also capable of passage through a valved cannula. The systems and methods disclosed herein overcome one or more of the deficiencies of the prior art.

SUMMARY

In one exemplary embodiment, the present disclosure describes an apparatus for treatment of an ocular condition of a patient, comprising a hollow elongate member sized to penetrate an eye of the patient. In one aspect, the elongate member includes a body portion and a distal tip. In one aspect, the body portion includes a proximal end, a distal end, and a first diameter, and defines a longitudinal axis. In one aspect, the distal tip extends from the distal end of the body portion and is arranged to treat tissue within the eye. In one aspect, the distal tip includes an inner tube and a second diameter. In one aspect, the distal tip is configured to transition between a first rigid orientation and a second less rigid orientation. In one aspect, the elongate member includes a lumen extending through the body portion and the distal tip, and the lumen is defined in part by the inner tube.

In another exemplary embodiment, the present disclosure describes a system for ophthalmic microsurgery, comprising an instrument tip sized to penetrate an eye of a patient. In one aspect, the instrument tip comprises a body portion including proximal end and a distal end, and the body portion defines a longitudinal axis. In one aspect, the instrument tip comprises a distal tip extending from to the distal end of the body portion, wherein the distal tip is arranged to treat tissue within the eye. In one aspect, the distal tip includes an inner tube, which is configured to transition between a first configuration before penetrating the eye and a second configuration after penetrating the eye. In one aspect, the instrument tip comprises a lumen extending through the body portion and the distal tip, and the lumen is defined in part by the inner tube. In one aspect, the instrument tip comprises a connector portion at the proximal end of the body portion. In one aspect, the system comprises a handle, and the connector portion is configured to couple the instrument tip to the handle. In one aspect, the system comprises a supply line (e.g., a vacuum line) coupled to the handpiece.

In another exemplary embodiment, the present disclosure describes a method for using an instrument in an eye during ophthalmic microsurgery, comprising positioning a tube of a valved cannula into the eye, the valved cannula including a slit allowing access into the tube. In one aspect, the method comprises positioning a distal tip of the instrument against the slit, the distal tip being configured to transition between a first configuration below a temperature threshold and a second configuration above the temperature threshold. In one aspect, the method comprises advancing the distal tip of the instrument through the slit while the distal tip is in the first configuration. In one aspect, the method comprises permitting the distal tip of the instrument to assume the second configuration within the eye. In one aspect, the distal tip includes an inner tube and a flexible outer sheath surrounding the inner tube, and the inner tube is more rigid in the first configuration and is less rigid in the second configuration. In one aspect, the method further comprises aspirating subretinal fluid from the eye through the distal tip as the distal tip is in the second configuration without injuring the retina and surrounding tissues. In one aspect, the method further comprises manipulating a retina of the eye with the distal tip as the distal tip is in the second configuration without injuring the retina and surrounding tissues.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately. For simplicity, in some instances the same reference numbers are used throughout the drawings to refer to the same or like parts.

The present disclosure relates generally to microsurgical instruments having variable stiffness, and in particular to variable stiffness cannulas for use with valved cannulas. In some instances, embodiments of the present disclosure are configured to be part of an ophthalmic surgical system. Instead of having a soft distal tip, the microsurgical instruments disclosed herein include a distal tip having variable stiffness. In some instances, the devices, systems, and methods disclosed herein include a distal instrument tip that is configured to undergo a state change with a change in temperature. For example, in one embodiment, the devices disclosed herein may be configured to be substantially rigid at a first temperature and be more flexible at a second, higher temperature. Thus, unlike conventional soft-tipped instruments, the devices disclosed herein may be capable of independent insertion through a valved cannula (e.g., at a first temperature) while maintaining the surgical functionality of a conventional soft-tip cannula (e.g., at a second, higher temperature). Therefore, the devices, systems, and methods disclosed herein may allow a surgeon to more efficiently and/or more easily perform procedures requiring the use of a "soft-tipped" surgical instrument.

Figure 1:
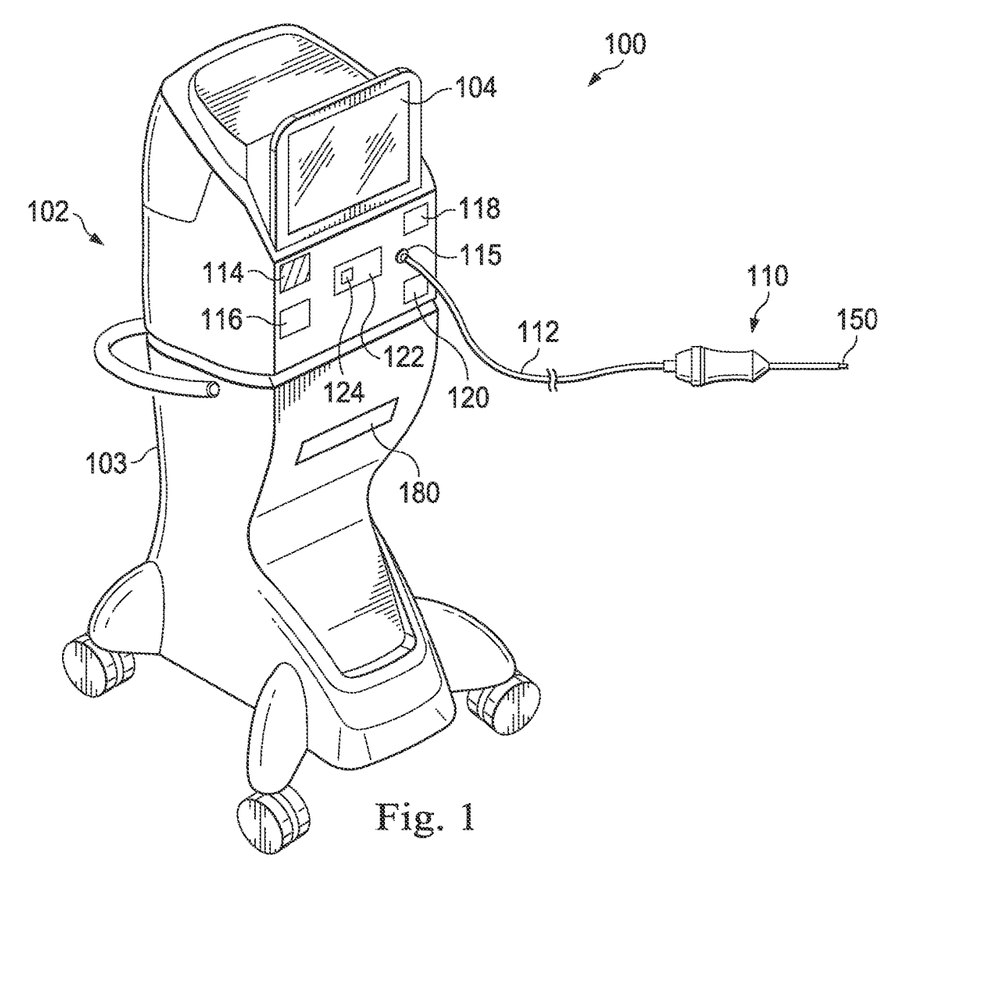
FIG. 1 illustrates a perspective view of a microsurgical system according to one embodiment of the present disclosure.

FIG. 1 illustrates a surgical system 100 according to an exemplary embodiment. Though the surgical system 100 shown in FIG. 1 is an ophthalmic microsurgical system, the surgical system 100 may be any microsurgical system. In some embodiments, the system 100 is capable of providing pneumatic drive pressure or electrically actuated cutter drive currents, voltages, and aspiration vacuum to a vitrectomy probe and irrigation fluid to an irrigation cannula in an ophthalmic surgical procedure. The system 100 may be capable of providing electrical power, ultrasound power, irrigation fluid, and aspiration vacuum to a probe 110 during an ophthalmic surgical procedure.

The surgical system 100 includes a console 102 that has a mobile base housing 103 and an associated display screen 104 showing data relating to system operation and performance during a surgical procedure. During ophthalmic surgery, a series of handpieces may be coupled to the system 100, typically via conventional supply lines 112 (e.g., comprising flexible plastic, silicone, or rubber tubing and/or electric cabling) fluidly coupled with a surgical cassette (not shown) to operatively connect to the system 100 through one or more ports 115. In some embodiments, the supply lines 112 comprise aspiration lines, power lines, and/or irrigation lines. One exemplary handpiece is the probe 110 that will be described in greater detail below with reference to FIG. 2.

The console 102 of the surgical system 100 includes features that may allow for control of the probe 110. For example, pneumatic and/or electrical supply lines 112 may couple the probe 110 to the console 102. In some embodiments, the supply lines 112 may facilitate control and monitoring to the probe 110 by also transmitting data between the probe 110 and the console 102. In other embodiments, data may be transferred wirelessly between the probe 110 and the console 102.

The console 102 further includes one or more processors 114 in communication with a memory 116. The processor 114 may have computer-instructions to control the probe 110, display information on the screen 104, and receive and process input commands and data. In some embodiments, the surgical system 100 includes a data transmission module 118. In some embodiments, the surgical system 100 may include a network interface 120 for communication with a network. In the pictured embodiment, the surgical system 100 includes a user interface 122 that enables the user to input data and/or command signals.

For example, in one embodiment, the user interface 122 may include a control element 124 that allows the user to trigger a state change in the probe 110. In some embodiments, the control element 124 comprises a button that may be depressed to activate the state change. In other embodiments, the control element 124 comprises a plurality of buttons with each button configured to activate and/or deactivate different functions of the probe 110. However, the control element 124 may comprise any of a variety of ON/OFF switches, buttons, toggles, wheels, or other user input devices. In some embodiments, the control element 124 may be additionally or alternatively disposed on the probe 110. These features facilitate control of the probe 110 during operation.

The processor 114 is typically an integrated circuit with power, input, and output pins capable of performing logic functions. For example, the processor 114 may perform logic functions based on inputs from the control element 124 to affect the state change of the probe 110. In some embodiments, the processor 114 controls the supply of power from a power source to the probe 110 and/or signal commands to the probe 110. In various embodiments, the processor 114 may be a targeted device controller or a microprocessor configured to control more than one component of the probe 110 or a combination thereof. The processor 114 may include one or more programmable processor units running programmable code instructions for controlling the probe 110, among other functions. For example, in some embodiments, the processor 114 can control the aspiration and/or backflush functions of the probe 110.

The processor 114 may be wirelessly coupled to a computer and/or other types of processor-based devices suitable for a variety of ocular applications. In various embodiments, the processor 114 can receive input data from a user, the control element 124, the probe 110, and/or various accessory devices via wireless or wired mechanisms. The processor 114 may use such input data to generate control signals to control or direct the operation of the probe 110. In some embodiments, the processor 114 is in direct wireless communication with the probe 110, and can receive data from and send commands to the probe 110.

The memory 116, which is typically a semiconductor memory such as Random Access Memory (RAM), Ferroelectric RAM (FRAM), or flash memory, interfaces with the processor 114. As such, the processor 114 can write to and read from the memory 116, and perform other common functions associated with managing semiconductor memory. For example, a series of tissue characterizations and/or command sequences can be stored in the memory 116.

The processor 114 and/or the memory 116 may also include software containing one or more algorithms defining one or more functions or relationships between command signals and input data (received from the user, the command element 124, and/or accessory devices). The algorithm may dictate activation or deactivation command protocols/signals (e.g., to the probe 110) depending on the received input data or mathematical derivatives thereof. For example, in some embodiments, the processor 114 includes logic algorithms that use input data from the control element 124 to activate and/or deactivate various components or functions of the probe 110. Thus, the processor 114 may be operable to selectively implement one or more control or logic algorithms to enable and/or inhibit the functionality of the probe 110. In some embodiments, the processor 114 may be re-programmed to selectively implement one or more particular control algorithms.

As mentioned above, in various embodiments, the probe 110 may be operatively coupled to the console 102 (and, in particular, the processor 114) by way of wired or wireless communication mechanisms. Contemplated wireless communication methods include, by way of nonlimiting example, cooperating transmitters and receivers positioned on various components of the probe 110 to allow remote communication with various components of the system 100. Thus, the data transmission module 118 may employ any of a number of different types of data transmission. In some embodiments, the data transmission module 118 may be activated to communicate the sensed data from the probe 110 to the processor 114 and/or the memory 116. In some embodiments, control signals or program algorithms may be transmitted to the data transmission module 118 from the user interface 122 and/or an external device to adjust the treatment settings/algorithms.

A variety of peripheral devices may also be coupled to the system 100, such as storage devices (hard disk drive, compact disc read-only memory (CD ROM) drive, etc.), printers, and other input/output devices. For example, in the pictured embodiment, the system 100 includes a sterile docking station 180 for the probe 110. The docking station 180 may be integrated with or coupled to the console 102, or may be a remote, stand-alone structure. In some embodiments, the docking station 180 functions as a temperature-controlled container configured to receive the probe 110 (or at least for the distal tip 150 of the probe 110) and regulate the temperature of the distal tip 150. The docking station 180 may operate as a cooler or refrigerator for the distal tip 150 in any of a variety of ways. For example, in one embodiment, the docking station 180 may be cooled using the Joule Thompson effect. In another embodiment, the docking station 180 may comprise a miniature refrigerator driven by gas pressure from the console 102 or a Peltier effect (e.g., an electrothermal cooler).

Figure 2:
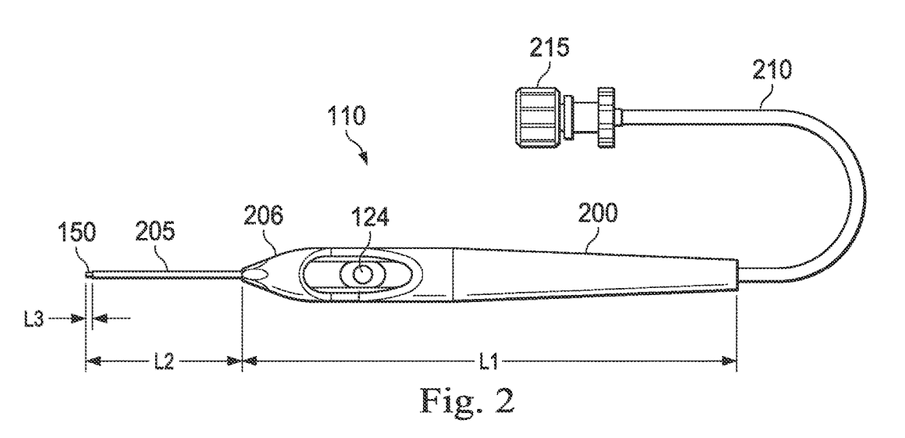
FIG. 2 illustrates a side view of an exemplary probe according to one embodiment of the present disclosure.

FIG. 2 illustrates a side view of the exemplary probe 110 according to one embodiment of the present disclosure. In the pictured embodiment, the probe 110 comprises a cannula, which may aspirating or non-aspirating. The exemplary probe 110 includes a proximal portion 200 and an instrument tip or distal portion 205, which terminates distally with the distal tip 150. In some instances, the distal portion 205 may be detachably coupled to the proximal portion 200. In some instances, a connector portion 206 forms part of the distal portion 205 and serves as a fastener to detachably couple the distal portion 205 to the proximal portion 200. The connector portion 206 may be shaped and configured to removably attach the distal portion 205 to the proximal portion 200 using one or more of a threaded engagement, a snap-fit engagement, a frictional engagement, and/or any other mechanism for temporarily connecting the distal portion 205 to the proximal portion 200. In other instances, the connector portion 206 forms part of the proximal portion 200. In other embodiments, the distal portion 205, the connector portion 206, and the proximal portion 200 together form an integral structure and cannot be easily separated from each other.

A length L1 of the proximal portion 200 (and the connector 206) may range from 75 to 100 millimeters (mm) For example, in one embodiment, the length L1 may be 93 mm. A length L2 of the distal portion 205 may range from 25 to 35 mm. The length L2 of the distal portion 205 may allow for the probe 110 to access the retina of an average patient's eye. For example, in one embodiment, the length L2 may be 34 mm. In some embodiments, a length L3 of the distal tip 150 may range from 1 mm to 5 mm. For example, in one embodiment, the length L3 may be 2 mm. These dimensions are supplied for exemplary purposes only, and are not intended to be limiting. Other dimensions are contemplated.

In the pictured embodiment, the proximal portion 200 includes the control element 124 to enable user control of various functions of the probe 110. The proximal portion 200 comprises a handle for the user to grasp while operating the probe 110. Such handles are known and are commonly referred to as extrusion handles. The proximal portion 200 is coupled to a supply line 210. In some embodiments, the supply line 210 is the same as the supply line 112 shown in FIG. 1. In other embodiments, the supply line 210 is coupled to the supply line 112 and/or the console 102 at a hub 215. In the case of an aspirating probe, the proximal portion or handle 200 may be hollow so that fluid, gas, and other material may flow through the proximal portion 200. In the case of a non-aspirating device, the proximal portion 200 may be solid or hollow as desired.

Figure 3:
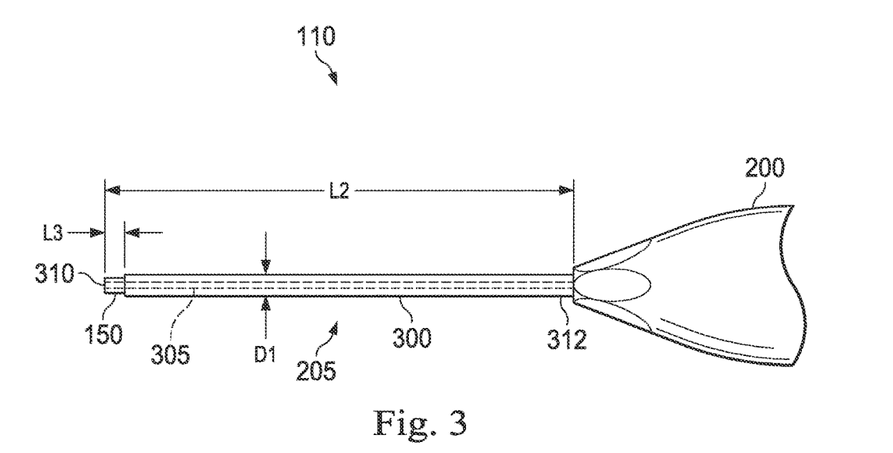
FIG. 3 illustrates a side view of an exemplary distal portion (and an exemplary connector portion) of the probe shown in FIG. 2.

FIG. 3 illustrates a side view of the probe 110 (with phantom lines), and in particular, the distal portion 205. The distal portion 205 comprises a hollow elongate member that includes a body portion 300 and the distal tip 150. The body portion 300 is adjacent the proximal portion 200, and the probe 110 terminates distally with the distal tip 150. The distal portion 205 includes a lumen 305 that extends through the distal tip 150 and the body portion 300. Fluids, gases, and other materials may flow from a distal end 310 of the probe 110 through the lumen 305. In some instances, the lumen 305 may extend proximally through the proximal portion 200 and couple to the supply line 210 (shown in FIG. 2). Although the distal portion 205 is depicted as having an elongate cylindrical shape, other shapes are contemplated.

The body portion 300 may have a substantially uniform cross-sectional diameter D1 from a proximal end 312 to the distal end 310 as shown in the pictured embodiment or may taper toward the distal tip 150. The diameter D1 may range from 0.3 mm to 1.5 mm. In one embodiment, the diameter D1 is 1.067 mm, (e.g., 19 gauge). In another embodiment, the diameter D1 is 0.305 mm, or 30 gauge. These dimensions are supplied for exemplary purposes only, and are not intended to be limiting. Other dimensions are contemplated. The body portion 300 may be formed of any suitable biocompatible material used in forming similar surgical instruments, such as, by way of non-limiting example, polymers and stainless steel.

Figure 4:
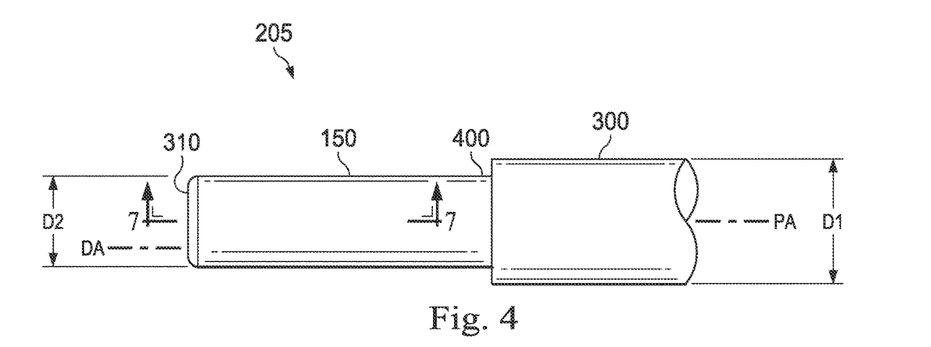
FIG. 4 illustrates a side view of an exemplary distal tip of the probe shown in FIG. 2 in a straight configuration according to one embodiment of the present disclosure.
Figure 5:
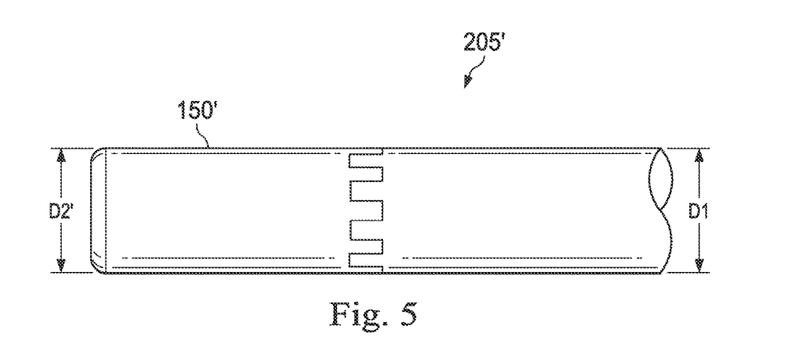
FIG. 5 illustrates another exemplary distal tip of the probe shown in FIG. 2 in a straight configuration according to one embodiment of the present disclosure.

FIGS. 4 and 5 illustrate detailed views of various embodiments of the distal tip 150. In particular, FIG. 4 illustrates a detailed view of the distal portion 205, and FIG. 5 illustrates a detailed view of an exemplary distal portion 205' according to another embodiment of the present disclosure. The distal tip 150 comprises a hollow, elongate structure extending distally from the body portion 300. In the pictured embodiment, the distal tip includes a substantially uniform cross-sectional diameter D2. In alternative embodiments, the diameter D2 may taper from a proximal end 400 of the distal tip 150 to the distal end 310. In the pictured embodiment, the diameter D2 of the distal tip 150 is smaller than the diameter D1 of the body portion 300. In other embodiments, as shown in FIG. 5, the diameter D2' of another exemplary distal tip 150' is substantially the same as the diameter D1 of the body portion 300. The diameter D2 may range from 0.1 mm to 1.5 mm. In the pictured embodiment in FIG. 4, the diameter D2 may be 0.8 mm. In the pictured embodiment in FIG. 5, the diameter D2' may be 1.067 mm. These dimensions are supplied for exemplary purposes only, and are not intended to be limiting. Other dimensions are contemplated.

Figure 6:
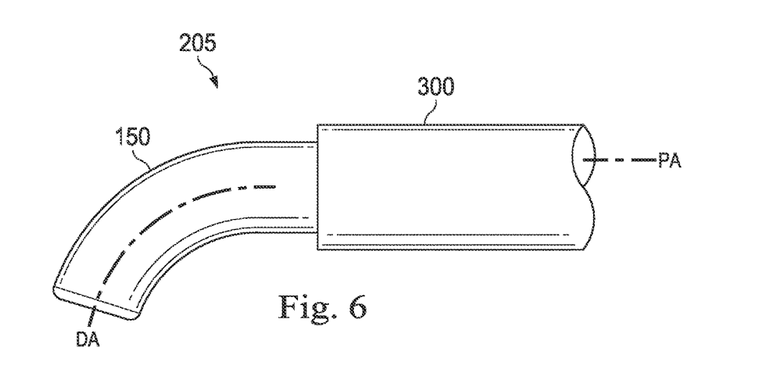
FIG. 6 illustrates a side view of the exemplary distal tip shown in FIG. 4 in a curved configuration according to one embodiment of the present disclosure.

As mentioned above, the distal tip 150 comprises an elongate, tubular structure with variable stiffness. FIGS. 4 and 6 illustrate the distal tip 150 in two different states of varying stiffness and/or shape. In particular, the distal tip 150 may be configured to have a more flexible and/or curved state at one temperature, as shown in FIG. 6, and a substantially rigid and straight state at another temperature, as shown in FIG. 4. In some embodiments, the distal tip 150 is configured to assume the more rigid, straight state at a first temperature, and to assume the more flexible, curved state at a second, higher temperature. For example, in one embodiment, the distal tip 150 will assume a rigid state below room temperatures (e.g., ranging from 15-27° Celsius) and will transition into or assume the more flexible and/or curved state at intraocular temperatures (e.g., 30-37° Celsius). In some embodiments, the distal tip 150 of the probe 110 may be stored in the docking station 180 shown in FIG. 1 to maintain the temperature of the distal tip 150 below room temperature to insure adequate stiffness for insertion through a valved cannula (e.g., the valved cannula 700 shown in FIG. 10).

In the rigid state, the distal tip 150 is configured to maintain its shape and to maintain the straight configuration shown in FIG. 4, in which a longitudinal axis DA of the distal tip 150 remains substantially aligned with a longitudinal axis PA of the body portion 300. In the flexible state, as shown in FIG. 6 the distal tip 150 may bend or curve relative to the body portion 300, and the longitudinal axis DA of the distal tip 150 may become non-aligned with the longitudinal axis PA of the body portion 300. In some embodiments, the distal tip 150 may be configured to assume a predetermined shape configuration in the flexible or curved state (e.g., the higher temperature state). In such embodiments, the distal tip 150 may be substantially rigid once it assumes the predetermined shape configuration (e.g., an arcuate shape). In the curved state, the distal tip 150 may be better suited to accessing parts of the posterior segment such as the subretinal space without causing inadvertent injury to the eye. The particular radius of the curvature may vary depending upon the desired application, with 12.5 being the most common. In alternative embodiments, the distal tip 150 may simply become more flexible in the flexible state and able to assume a variety of curvatures (e.g., with the application of external forces against the distal tip 150).

Figure 7:
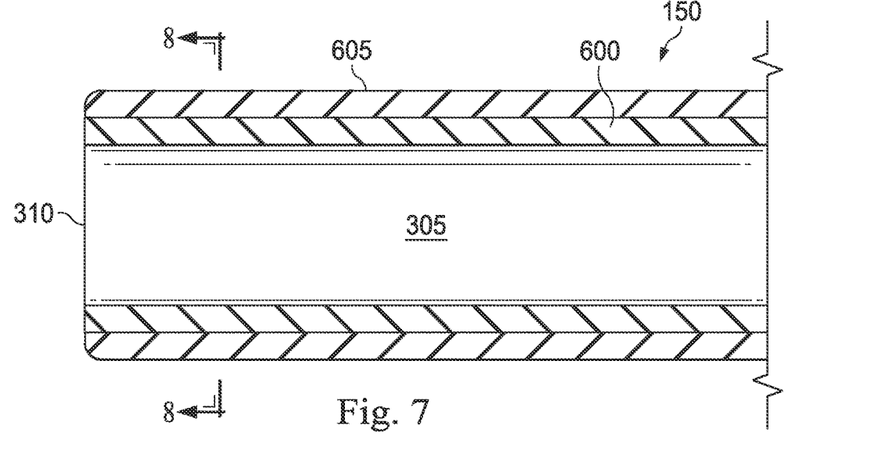
FIG. 7 illustrates a cross-sectional view of an exemplary distal tip taken along line 7-7 shown in FIG. 4 according to one embodiment of the present disclosure.
Figure 8:
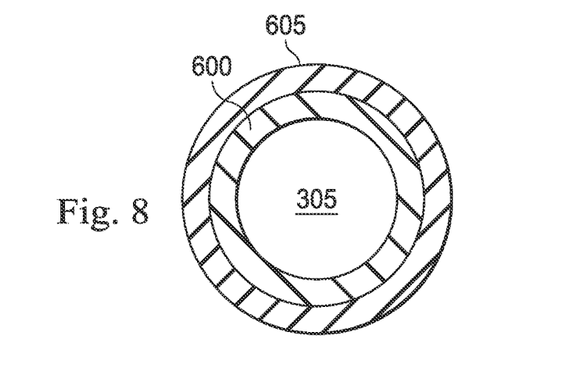
FIG. 8 illustrates a cross-sectional view of an exemplary distal tip taken along line 8-8 shown in FIG. 7 according to one embodiment of the present disclosure.

FIG. 7 illustrates a cross-sectional view of the distal tip 150 taken along the line 7-7 in FIG. 4 according to one embodiment of the present disclosure. FIG. 8 illustrates a cross-sectional view of the distal tip 150 taken along the line 8-8 shown in FIG. 7. As shown in FIGS. 7 and 8, the distal tip 150 comprises an inner tube 600 and an outer sheath 605.

The inner tube 600 defines the lumen 305 at the distal tip 150. In some embodiments, as described above, the distal tip 150 of the probe 110 is configured to undergo state changes in response to the ambient temperature surrounding the distal tip 150. This ability to shift through states of varying stiffness (and/or different curvatures) may arise from the state change properties of the inner tube 600. In alternative embodiments, the distal tip 150 comprises a unitary polymeric tube that can undergo state changes as described below in relation to the inner tube.

The inner tube 600 is constructed from a structurally deformable biocompatible material that can elastically or plastically deform without compromising its integrity. The inner tube 600 may be made from a shape memory material, such as Nitinol, or other biocompatible material having the requisite state change properties. For example, other materials having shape memory characteristics, such as particular metal alloys, may also be used. In some embodiments, the inner tube 600 is a solid, continuous tube. In other embodiments, the inner tube 600 is fenestrated and/or includes cut-out features. The shape memory materials allow the inner tube 600 to be in a straight, rigid configuration during delivery through a valved cannula (e.g., a valved cannula 700 shown in FIG. 10) into an eye and to assume (and, in some embodiments, maintain) its more flexible or curved configuration inside the eye after the delivery process. Thus, in some embodiments, the distal tip 150 is configured to be in a more rigid, straight configuration while being inserted through a cannula into the eye, and to assume a curved, more flexible configuration once it enters the eye.

The outer sheath 605 surrounds the inner tube 600. The outer sheath 605 may be formed of any of a variety of soft, flexible, biocompatible materials, including, by way of non-limiting example, polymers, silicone, polyimide, and Polytetrafluoroethylene (PTFE). For example, in some embodiments, the outer sheath 605 comprises a soft polymer layer that is overmolded onto the inner tube 600. Although the outer sheath 605 is shown concentrically arranged with the inner tube 600, in some embodiments, the outer sheath 605 may encase the inner tube 600 (e.g., may form a polymeric layer coating the inner and outer surfaces of the inner tube 600). The outer sheath 605 may serve as a buffer between the structures of the eye and the inner tube 600 to prevent accidental injury to the delicate internal structures of the eye caused by contact with the inner tube 600. Although the inner tube 600 and the outer sheath 605 are shown as having a circular cross-sectional profile in FIG. 8, the inner tube 600 and the outer sheath 605 may have any of a variety of cross-sectional shapes, including, without limitation, ovoid, triangular, and rhomboid. Some embodiments lack the outer sheath 605 (e.g., the distal tip 150 may comprise a one piece Nitinol cannula or alternative material cannula).

Figure 9:
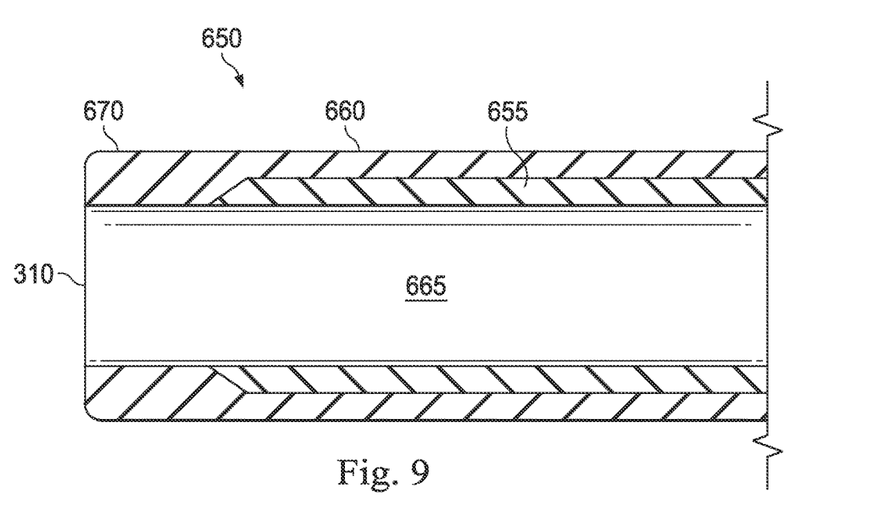
FIG. 9 illustrates a cross-sectional view of another exemplary distal tip according to one embodiment of the present disclosure.

In the pictured embodiment in FIG. 7, both the inner tube 600 and the outer sheath 605 terminate (distally) at the distal end 310 of the probe 110. However, in alternative embodiments, the inner tube may terminate proximal to the distal end 310. In this regard, FIG. 9 illustrates an exemplary distal tip 650 that is substantially similar to the distal tip 150 described above except for the differences described herein. The distal tip 650 includes an inner tube 655 that terminates proximal to an outer sheath 660. The outer sheath 660 thickens at the distal end 310 that defines the distal-most part of a lumen 665 of the distal tip 650, and to provide a soft, pliable, annular thickened portion or nub 670 for the probe 110. In some embodiments, the nub 670 may act as a distance guide, allowing the surgeon to position the harder portion of the distal tip 650 (i.e., the inner tube 655) repeatedly at the same distance from the retina.

Figure 10:
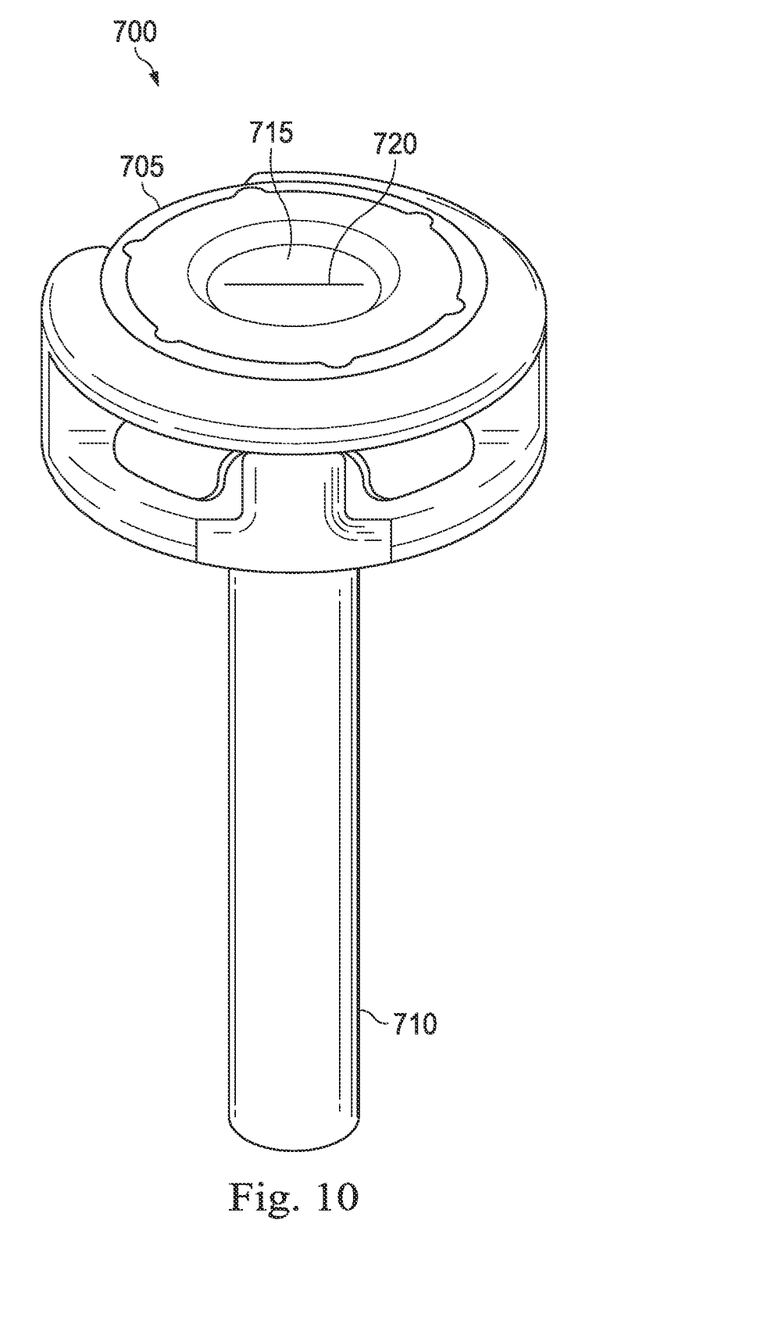
FIG. 10 illustrates an exemplary valved cannula according to one embodiment of the present disclosure.

FIG. 10 illustrates an exemplary valved cannula 700 according to one embodiment of the present disclosure. The valved cannula 700 includes a hub 705 connected to a hollow tube 710. The hub 705 of the valved cannula 700 includes a silicone diaphragm 715 having a slit 720. The slit 720 provides an opening into the tube 710 through which a surgical instrument such as the probe 110 can be inserted.

Figure 11:
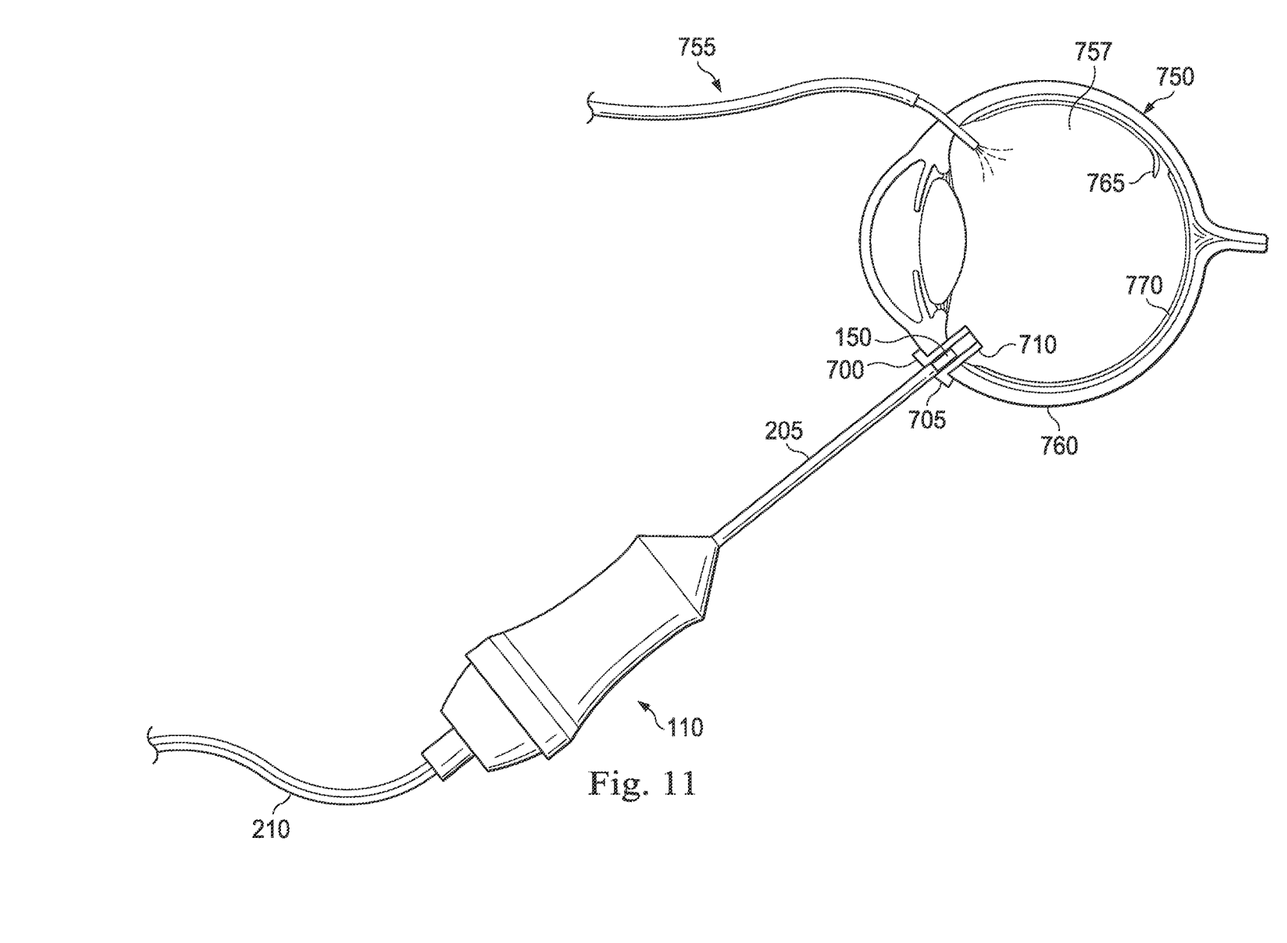
FIG. 11 illustrates a partially cross-sectional view of an exemplary probe being inserted through an exemplary valved cannula into an eye according to an exemplary method of the present disclosure.
Figure 12:
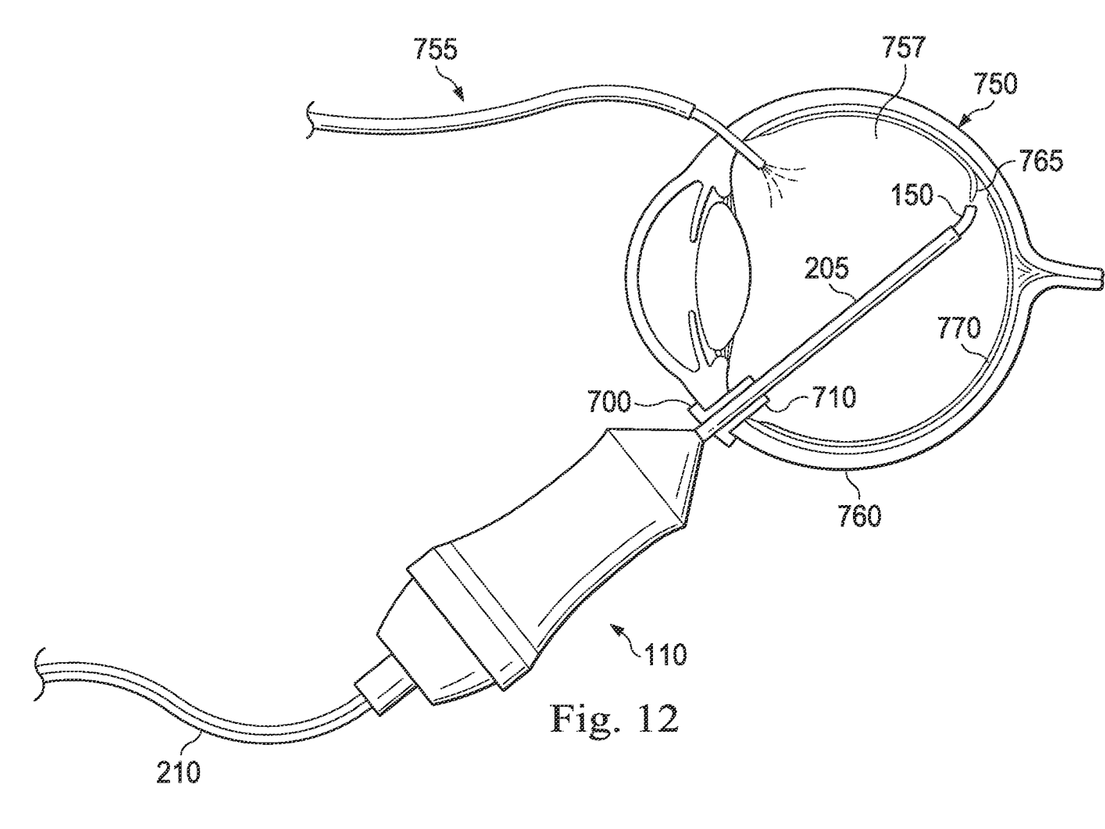
FIG. 12 illustrates a partially cross-sectional view of the exemplary probe shown in FIG. 11 advanced toward the retina of an eye according to an exemplary method of the present disclosure.
Figure 13:
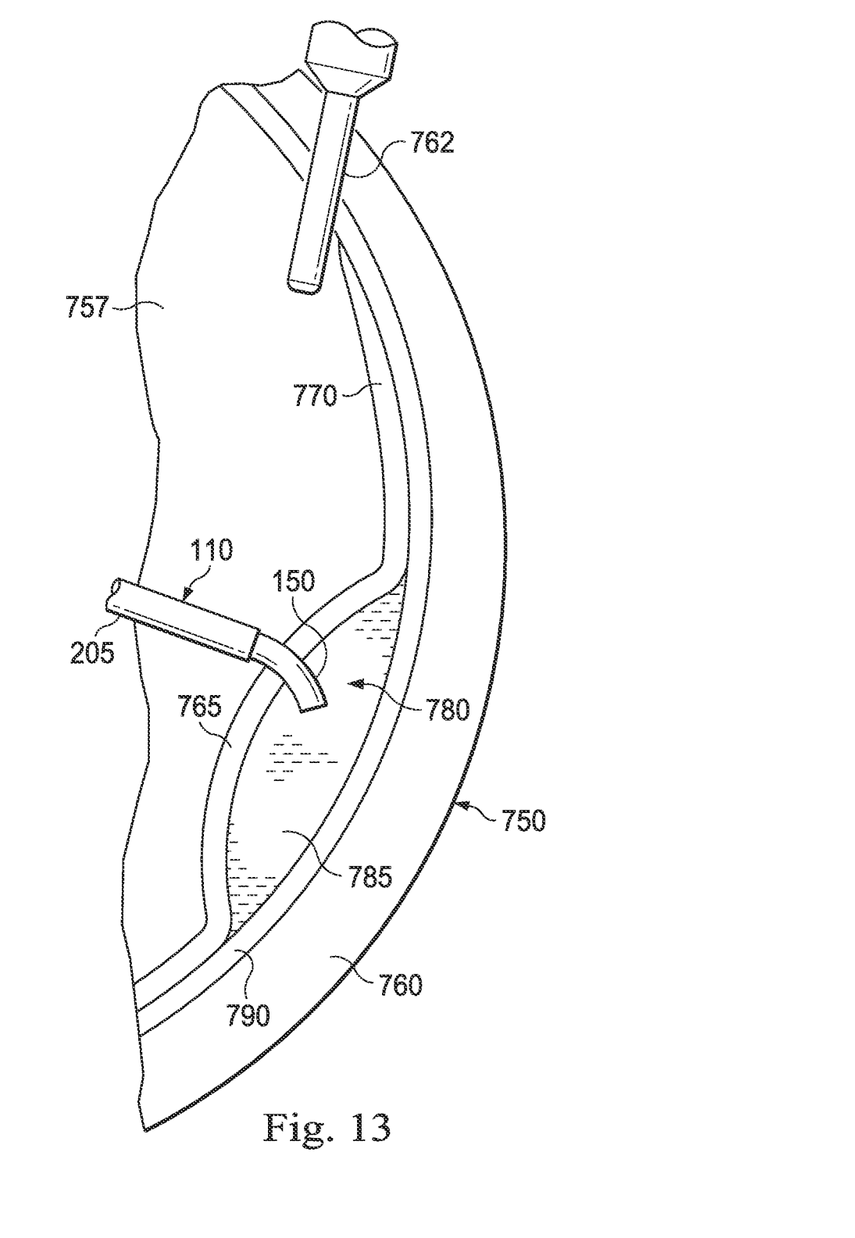
FIG. 13 illustrates a partially cross-sectional view of an exemplary distal tip within the subretinal space of an eye according to an exemplary method of the present disclosure.

FIGS. 11 and 12 illustrate partially cross-sectional views of an eye 750 undergoing a procedure involving the surgical system 100, the probe 110, and an infusion line or infusion cannula 755 according to an exemplary method of the present disclosure. Both the probe 110 and the infusion cannula 755 may be coupled to a console, such as the console 102 shown in FIG. 1. In FIG. 11, the probe 110 and the infusion cannula 755 are inserted through a sclera 760 and into a vitreous chamber 757 of the eye 750. The infusion cannula 755 is a specialized type of probe used to deliver replacement fluid or irrigation fluid into the vitreous chamber 757 during posterior segment procedures. During a posterior segment procedure, a surgeon typically inserts a valved cannula such as the valved cannula 700 into the eye 750 via an incision through the sclera 760. The surgeon typically also inserts a fiber optic light source and the infusion cannula 755 into the eye via similar incisions. In some instances, while viewing the posterior segment under a microscope and with the aid of a light source (e.g., a light source 762 as shown in FIG. 13), the surgeon first cuts and aspirates away vitreous humor (and/or membranes) using a vitrectomy probe (not shown) to gain access to the area of interest (e.g., the site of a retinal detachment or tear 765 on a retina 770). The surgeon may also use the vitrectomy probe to remove any membrane that has contributed to the retinal detachment or tear 765. During the surgery, a saline solution may be infused into the eye via the infusion cannula 755 to maintain the appropriate intraocular pressure. A pressure level of the irrigation fluid may be increased or decreased by a surgical system 100.

After the vitreous is removed, the surgeon may insert the probe 110 through the slit 720 of the valved cannula 700 (shown in FIG. 10). As described above, at a first, lower temperature such as room temperature or below room temperature (e.g., the distal tip may be pre-cooled below temperature), the distal tip 150 of the probe 110 is in a more rigid, straight configuration (as shown in FIG. 4). Therefore, as the surgeon contacts the slit 720 of the valved cannula 700 with the probe 110, the distal tip 110 is in a rigid, straight configuration. Because the distal tip 110 is in a more rigid, straight configuration at or below room temperature, the distal tip 110 can open the slit 720 to pass through the hub 705 and into the tube 710 without the application of undue pressure on the valved cannula 700. As the distal tip 110 passes into the vitreous chamber 757 of the eye 400, the temperature surrounding the distal tip 110 increases to the intraocular temperature (e.g., 25-37° Celsius given that the infusion fluid temperature is generally approximately 25° Celsius and body temperature is generally 37° Celsius).

FIG. 12 illustrates the distal tip 110 positioned within the vitreous chamber 757 of the eye 750 and adjacent the retinal detachment or tear 765. As shown in FIG. 12, as the temperature surrounding the distal tip 110 increases to the intraocular temperature, the distal tip 110 undergoes a state transformation or a state change to the more flexible and/or curved state, thereby enabling the surgeon to more easily use the probe 110 under the retinal detachment 765 with a lower risk of inadvertently injuring the retina or retinal pigment epithelium 770.

For example, as illustrated in FIG. 13, the surgeon may insert the distal tip 150 of the probe 110 underneath the retinal detachment or tear 765 and into a subretinal space 780 to aspirate subretinal fluid 785, thereby causing the retina 770 to return to its normal anatomical position on the eye 750. In FIG. 13, the light source 762 is shown inserted into the vitreous chamber 757. In some instances, the distal tip 150 transitions to a curved shape configured to allow easier access into the subretinal space when the distal tip 150 assumes the curved and/or more flexible state of the distal tip 150 at the higher temperature (e.g., the intraocular temperature). In some embodiments, the surgeon may use the distal tip 150 to reposition the retinal detachment or tear 765 against the retinal pigment epithelium. In some embodiments, a diathermy probe, laser, and/or adhesive (not shown) is subsequently used to fuse the retinal detachment or tear 765 in place against a choroid 790.

The various probe embodiments described herein utilize distal tips having the ability to be in a more rigid or straight condition while outside the eye and to be in a more flexible or curved condition when inside the eye. In some embodiments, the probe can undergo a state change or transformative shape change in response to shifts in temperature. In particular, in some embodiments, when the distal tip approaches a threshold temperature or transition temperature, the distal tip undergoes a state change or shape change. For example, in one embodiment, the threshold temperature is the intraocular temperature (e.g., of a typical human eye), and the distal tip transitions from a more rigid condition at room temperature to a more flexible, curved condition when the distal tip heats up to the intraocular temperature. In one aspect, the probes described herein can assume the more rigid and/or straight condition when below the threshold temperature (e.g., at room temperature) to facilitate potentially easier insertion into an eye through a valved cannula, and can assume the more flexible and/or curved condition when above the threshold temperature within the eye (e.g., at intraocular temperature) to enable potentially safer manipulation of the retina and insertion through a retinal defect into the subretinal space.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

I claim:

1. An apparatus for treatment of an ocular condition of a patient by physically manipulating eye tissue and by aspirating fluid from an eye of the patient, the apparatus comprising:
    a hollow elongate member sized to penetrate and treat the eye of the patient, including:
        a body portion including a proximal end, a distal end, and a first diameter, the body portion defining a longitudinal axis;
        a distal retinal-treatment tip extending from the distal end of the body portion and arranged to treat retinal tissue within the eye, the distal retinal-treatment tip is a unitary polymeric tube with a second diameter, the second diameter being sized to allow at least a portion of the distal retinal-treatment tip to be inserted under a retinal detachment to treat the retinal tissue, wherein the unitary polymeric tube goes through a material state change transition between a first rigid configuration at a first temperature and a second less rigid configuration at an intraocular temperature, wherein the first temperature is in a range of 15 to 27 degrees Celsius, the unitary polymeric tube is straight in the first configuration and curved relative to the body portion longitudinal axis in the second configuration; and
        an aspiration lumen extending through the body portion and the distal retinal-treatment tip, wherein the lumen is defined in part by the unitary polymeric tube and includes an opening at an end of the distal retinal-treatment tip along a central axis of the unitary polymeric tube to aspirate fluid from the eye.

2. The apparatus of claim 1, further comprising a connector portion at the proximal end of the body portion, the connector portion configured to selectively couple the hollow elongate member to a handle.

3. The apparatus of claim 1, wherein the first diameter and the second diameter are substantially equal.

4. The apparatus of claim 1, wherein the first diameter is larger than the second diameter.

5. The apparatus of claim 1, wherein the unitary polymeric tube is formed of a shape memory material.

6. The apparatus of claim 5, wherein the unitary polymeric tube assumes the first rigid configuration below a threshold temperature, and the unitary polymeric tube assumes the second less rigid configuration above the threshold temperature.

7. The apparatus of claim 1, wherein the distal retinal-treatment tip includes an outer sheath surrounding and disposed on an outer surface of the unitary polymeric tube.

8. The apparatus of claim 7, wherein the outer sheath is formed of a flexible material suitable for engaging sensitive retinal tissue while minimizing trauma.

9. The apparatus of claim 7, wherein both the unitary polymeric tube and the outer sheath extend to a distal end of the hollow elongate member.

10. The apparatus of claim 7, wherein the unitary polymeric tube terminates proximal to a distal end of the hollow elongate member, and the outer sheath extends distal to the unitary polymeric tube to form a annular, pliable nub at a distal end of the hollow elongate member.

11. The system of claim 1, wherein the intraocular temperature is in a range of 30 to 37 degrees Celsius.

12. A system for ophthalmic microsurgery, comprising:
    an instrument tip sized to penetrate an eye of a patient and aspirate fluid from below retinal tissue in the eye of the patient, the instrument tip comprising:
        a body portion including a proximal end and a distal end, the body portion defining a longitudinal axis;
        a distal retinal-treatment tip extending from the distal end of the body portion and arranged to treat the retinal tissue within the eye, the distal retinal-treatment tip is a unitary polymeric tube and is sized to allow at least a portion of the distal retinal-treatment tip to be inserted under a retinal detachment to treat the retinal tissue, wherein the unitary polymeric tube goes through a material state change transition between a first rigid configuration at a first temperature before penetrating the eye and a second less rigid configuration at an intraocular temperature after penetrating the eye, wherein the first temperature is in a range of 15 to 27 degrees Celsius, the unitary polymeric tube is straight in the first configuration and curved relative to the body portion longitudinal axis in the second configuration;

an aspiration lumen extending through the body portion and the distal retinal-treatment tip, wherein the lumen is defined in part by the unitary polymeric tube and includes an opening at an end of the distal retinal-treatment tip along a central axis of the unitary polymeric tube to aspirate fluid from the eye; and a connector portion at the proximal end of the body portion;

a handle, wherein the connector portion is configured to couple the instrument tip to the handle; and an aspiration line coupled to the handpiece.

13. The system of claim 12, wherein the unitary polymeric tube is formed of a shape memory material.

14. The system of claim 12, further comprising a docking station structurally arranged to receive the distal retinal-treatment tip and maintain the distal retinal-treatment tip at or below the first temperature.

15. The system of claim 12, wherein the distal retinal-treatment tip includes a flexible outer sheath surrounding the unitary polymeric tube.

16. The system of claim 12 wherein the intraocular temperature is in a range of 30 to 37 degrees Celsius.

* * * * *